US00PP24385P2

(12) United States Plant Patent
Unger

(10) Patent No.: US PP24,385 P2
(45) Date of Patent: Apr. 15, 2014

(54) EUPHORBIA PLANT NAMED 'WESEUSOPI'

(50) Latin Name: *Chamaesyce hypericifolia*
Varietal Denomination: Weseusopi

(71) Applicant: Christian Unger, Worms (DE)

(72) Inventor: Christian Unger, Worms (DE)

(73) Assignee: Gartenbau und Spezialkulturen Westhoff GbR, Südlohn (DE)

( * ) Notice: Subject to any disclaimer, the term of this patent is extended or adjusted under 35 U.S.C. 154(b) by 0 days.

(21) Appl. No.: 13/573,842

(22) Filed: Oct. 8, 2012

(51) Int. Cl.
*A01H 5/00* (2006.01)

(52) U.S. Cl.
USPC ..... Plt./302

(58) Field of Classification Search
USPC ..... Plt./302
See application file for complete search history.

*Primary Examiner* — Kent L Bell
(74) *Attorney, Agent, or Firm* — C. A. Whealy

(57) ABSTRACT

A new and distinct cultivar of *Euphorbia* plant named 'Weseusopi', characterized by its compact, upright, outwardly spreading and mounding plant habit; moderately vigorous growth habit; freely branching habit; green-colored leaves with dark purple-colored spots; and numerous white and red purple-colored flowers.

3 Drawing Sheets

Botanical designation: *Chamaesyce hypericifolia.*
Cultivar denomination: 'WESEUSOPI'.

BACKGROUND OF THE INVENTION

The present invention relates to a new and distinct cultivar of *Euphorbia* plant, botanically known as *Chamaesyce hypericifolia* and hereinafter referred to by the name 'Weseusopi'.

The new *Euphorbia* plant is a product of a planned breeding program conducted by the Inventor in Worms, Germany. The objective of the breeding program is to create new compact *Euphorbia* plants with dark-colored leaves and freely flowering habit.

The new *Euphorbia* plant originated from a cross-pollination in July, 2009 in Worms, Germany of a proprietary selection of *Chamaesyce hypericifolia* identified as code number CH07-04, not patented, as the female, or seed, parent with a proprietary selection of *Chamaesyce hypericifolia* identified as code number CH07-11, not patented, as the male, or pollen, parent. The new *Euphorbia* plant was discovered and selected by the Inventor as a single flowering plant within the progeny of the stated cross-pollination in a controlled greenhouse environment in Worms, Germany in May, 2010.

Asexual reproduction of the new *Euphorbia* plant by vegetative cuttings in a controlled greenhouse environment in Worms, Germany since October, 2010 has shown that the unique features of this new *Euphorbia* plant are stable and reproduced true to type in successive generations.

SUMMARY OF THE INVENTION

Plants of the new *Euphorbia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Weseusopi'.

These characteristics in combination distinguish 'Weseusopi' as a new and distinct *Euphorbia* plant:

1. Compact, upright, outwardly spreading and mounding plant habit.
2. Moderately vigorous growth habit.
3. Freely branching habit.
4. Green-colored leaves with dark purple-colored spots.
5. Numerous white and red purple-colored flowers.

Plants of the new *Euphorbia* can be compared to plants of the female parent selection. Plants of the new *Euphorbia* differ primarily from plants of the female parent selection in growth habit as plants of the new *Euphorbia* are more compact than and not as vigorous as plants of the female parent selection.

Plants of the new *Euphorbia* can be compared to plants of the male parent selection. Plants of the new *Euphorbia* differ primarily from plants of the male parent selection in the following characteristics:

1. Plants of the new *Euphorbia* are more freely branching than plants of the male parent selection.
2. Plants of the new *Euphorbia* have green-colored leaves with dark purple-colored spots whereas plants of the male parent selection have green-colored leaves without spots.

Plants of the new *Euphorbia* can be compared to plants of *Chamaesyce hypericifolia* 'Diamond Fizz', not patented. Plants of the new *Euphorbia* differ from plants of 'Diamond Fizz' in the following characteristics:

1. Plants of the new *Euphorbia* are more compact than and not as vigorous as plants of 'Diamond Fizz'.
2. Plants of the new *Euphorbia* are denser than and not as open as plants of 'Diamond Fizz'.
3. Plants of the new *Euphorbia* have green-colored leaves with dark purple-colored spots whereas plants of 'Diamond Fizz' have green-colored leaves without spots.
4. Plants of the new *Euphorbia* and 'Diamond Fizz' differ in flower color as plants of 'Diamond Fizz' have solid white-colored flowers.

BRIEF DESCRIPTION OF THE PHOTOGRAPHS

The accompanying colored photographs illustrate the overall appearance of the new *Euphorbia* plant showing the colors as true as it is reasonably possible to obtain in colored reproductions of this type. Colors in the photographs may differ slightly from the color values cited in the detailed botanical description which accurately describe the colors of the new *Euphorbia* plant.

The photograph on the first sheet is a side perspective view of a typical flowering plant of 'Weseusopi' grown in a container.

The photograph on the second sheet is a close-up view of the upper (left) and lower (right) surfaces of typical leaves of 'Weseusopi'.

The photograph on the third sheet is a close-up view of typical flowers of 'Weseusopi'.

DETAILED BOTANICAL DESCRIPTION

The aforementioned photographs and following observations, measurements and values describe plants grown in 12-cm containers during the summer in a glass-covered greenhouse in Südlohn-Oeding, Germany and under cultural practices typical of commercial *Euphorbia* production. During the production of the plants, day temperatures ranged from 20° C. to 25° C., night temperatures ranged from 16° C. to 18° C. and light levels ranged from 3,000 to 50,000 lux. Plants were pinched one time and were four months old when the photographs and description were taken. In the following description, color references are made to The Royal Horticultural Society Colour Chart, 2001 Edition, except where general terms of ordinary dictionary significance are used.

Botanical classification: *Chamaesyce hypericifolia* 'Weseusopi'.

Parentage:

*Female, or seed, parent.*—Proprietary selection of *Chamaesyce hypericifolia* identified as code number CH07-04, not patented.

*Male, or pollen, parent.*—Proprietary selection of *Chamaesyce hypericifolia* identified as code number CH07-11, not patented.

Propagation:

*Type.*—By vegetative cuttings.

*Time to initiate roots, summer.*—About 20 days at temperatures of about 20° C.

*Time to initiate roots, winter.*—About 24 days at temperatures of about 20° C.

*Time to produce a rooted young plant, summer.*—About four weeks at temperatures of about 20° C.

*Time to produce a rooted young plant, winter.*—About five weeks at temperatures of about 20° C.

*Root description.*—Medium in thickness, fibrous; creamy white in color.

*Rooting habit.*—Moderately freely branching; medium density.

Plant description:

*Plant form and growth habit.*—Compact, upright, outwardly spreading and mounding plant habit; dense and bushy; broad inverted triangle; moderately vigorous growth habit.

*Branching habit.*—Freely branching habit; plants with about two to three lateral branches developing per node; pinching enhances lateral branch development.

*Plant height.*—About 20 cm.

*Plant diameter.*—About 33 cm.

*Lateral branch description.*—Length: About 11.8 cm. Diameter: About 1.6 mm. Internode length: About 3.7 cm. Strength: Moderately strong. Angle: About 45° from stem axis. Texture: Smooth, glabrous. Color: Close to 146A; at the nodes, close to 184B.

Foliage description:

*Arrangement.*—Opposite; simple.

*Length.*—About 2.4 cm.

*Width.*—About 1 cm.

*Shape.*—Lanceolate to oblong.

*Apex.*—Acute.

*Base.*—Obtuse.

*Margin.*—Entire.

*Texture, upper and lower surfaces.*—Slightly pubescent.

*Venation.*—Pinnate, arcuate.

*Color.*—Developing leaves, upper surface: Close to 146A; random spots, close to 187C. Developing leaves, lower surface: Close to 137B; random spots, close to 187C. Fully developed leaves, upper surface: Close to 137A; random spots, close to 187C; venation, close to 137A or 187C. Fully developed leaves, lower surface: Close to 147B; random spots, close to 187C; venation, close to 147B or 187C.

*Petioles.*—Length: About 2.2 cm. Diameter: About 0.8 mm. Texture, upper and lower surfaces: Tomentous. Color, upper surface: Close to 146B. Color, lower surface: Close to 146C.

Inflorescence description:

*Flower arrangement and flowering habit.*—Single rotate flowers arranged in terminal clusters; very freely flowering with numerous flower buds and flowers per plant; flowers face upright and outwardly.

*Fragrance.*—None detected.

*Natural flowering season.*—Plants flower naturally from April to frost in Germany; flowering continuous during this period.

*Flower longevity on the plant.*—About one week; flowers not persistent.

*Flower diameter.*—About 1.5 cm.

*Flower depth (height).*—About 9 mm.

*Flower buds.*—Height: About 2.9 mm. Diameter: About 1.4 mm. Shape: Ovoid. Color: Close to 137C; margin, close to 155A to 155B.

*Floral bracts.*—Quantity per flower: Two to three. Length: About 7.25 mm. Width: About 2.5 mm. Shape: Oblanceolate. Apex: Cuspidate. Base: Attenuate. Margin: Entire. Texture, upper and lower surfaces: Smooth, glabrous. Aspect: Upright to horizontal. Color: When opening, upper surface: Close to N155A to N155B. When opening, lower surface: Close to N155A to N155B; streaks towards the base, close to 63C. Fully opened, upper surface: Close to N155A to N155B; with development, towards the base, close to N66A. Fully opened, lower surface: Close to N66A. Petioles: Length: About 1.3 mm. Diameter: Less than 1 mm. Texture, upper and lower surfaces: Smooth, glabrous. Color, upper and lower surfaces: Close to 138C.

*Peduncles.*—Length: About 2 mm. Diameter: Less than 1 mm. Strength: Strong, flexible. Texture: Smooth, glabrous. Color: Close to 138A.

*Cyathia.*—Quantity per flower: One or two. Length: About 3.5 mm. Diameter: About 1.5 mm. Shape: Roughly oval. Aspect: Upright. Color, immature and mature: Close to 137C.

*Nectaries.*—Nectary development has not been observed on plants of the new *Euphorbia*.

*Reproductive organs.*—Androecium: Quantity per cyathium: About three. Filament length: About 1 mm. Filament color: Close to NN155D. Anther length: Less than 1 mm. Anther shape: Rounded. Anther color: Close to 18D. Pollen amount: None observed. Gynoecium: Quantity per cyathia: About six. Pistil length: About 2 mm. Style length: About 2 mm. Style color: Close to NN155D. Stigma shape: Branched. Stigma color: Close to NN155D. Ovary color: Greenish. Seeds and fruits: Seed and fruit development have not been observed on plants of the new *Euphorbia*.

Temperature tolerance: Plants of the new *Euphorbia* have been observed to have tolerate temperatures ranging from about 8° C. to about 30° C.

Pathogen & pest resistance: Plants of the new *Euphorbia* have not been observed to be resistant to pathogens and pests common to *Euphorbia* plants.

It is claimed:

1. A new and distinct *Euphorbia* plant named 'Weseusopi' as illustrated and described.

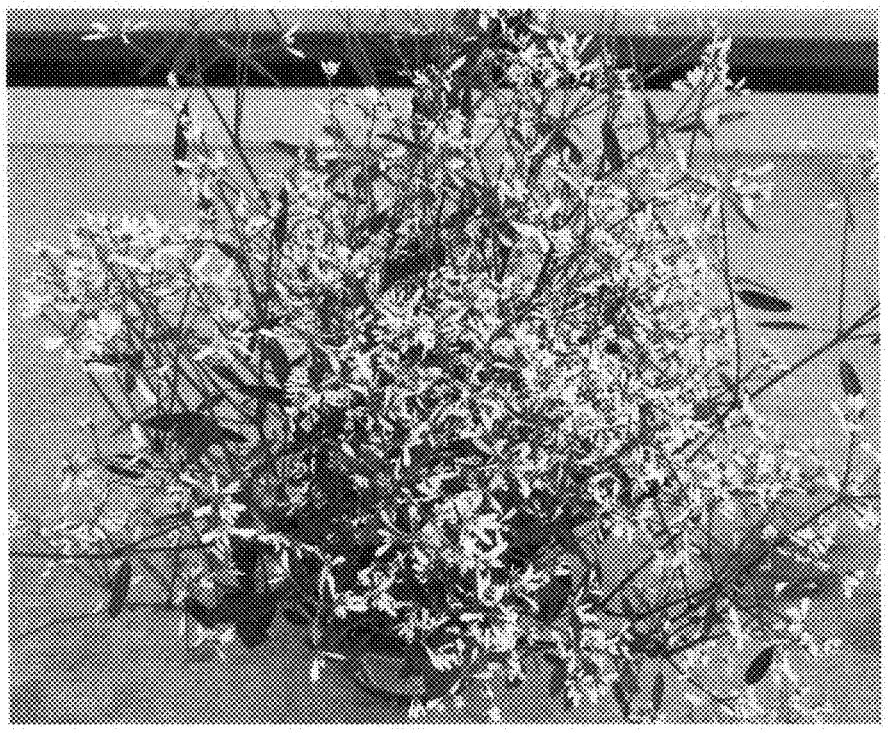

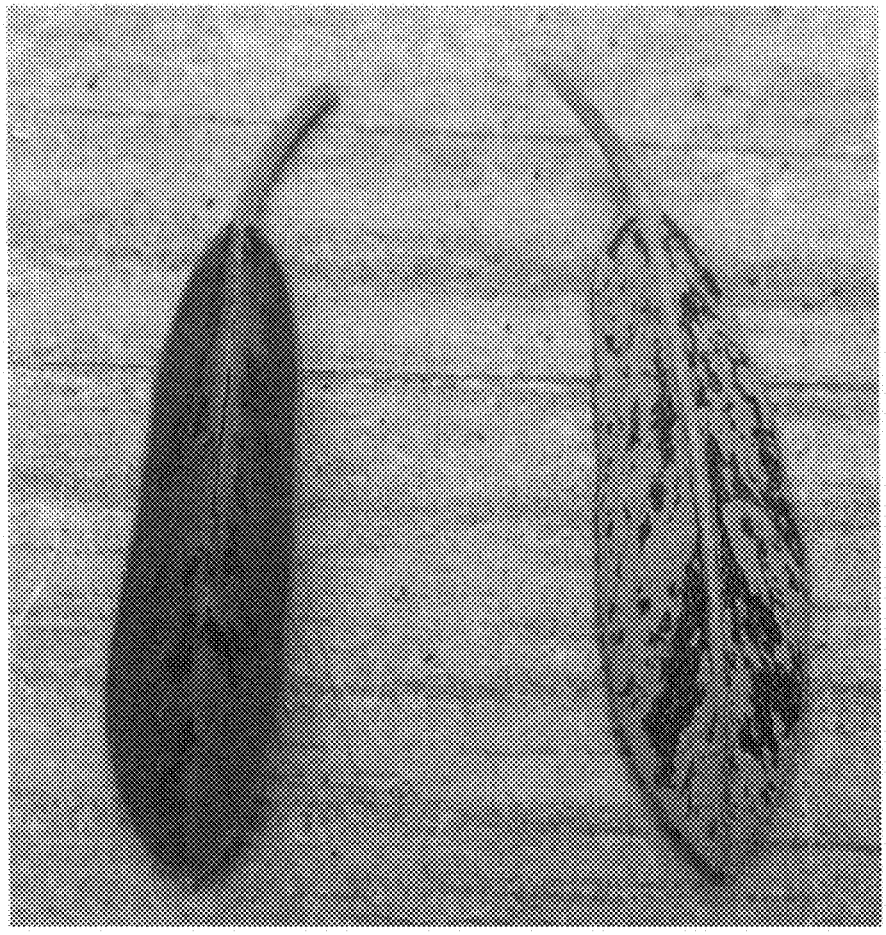

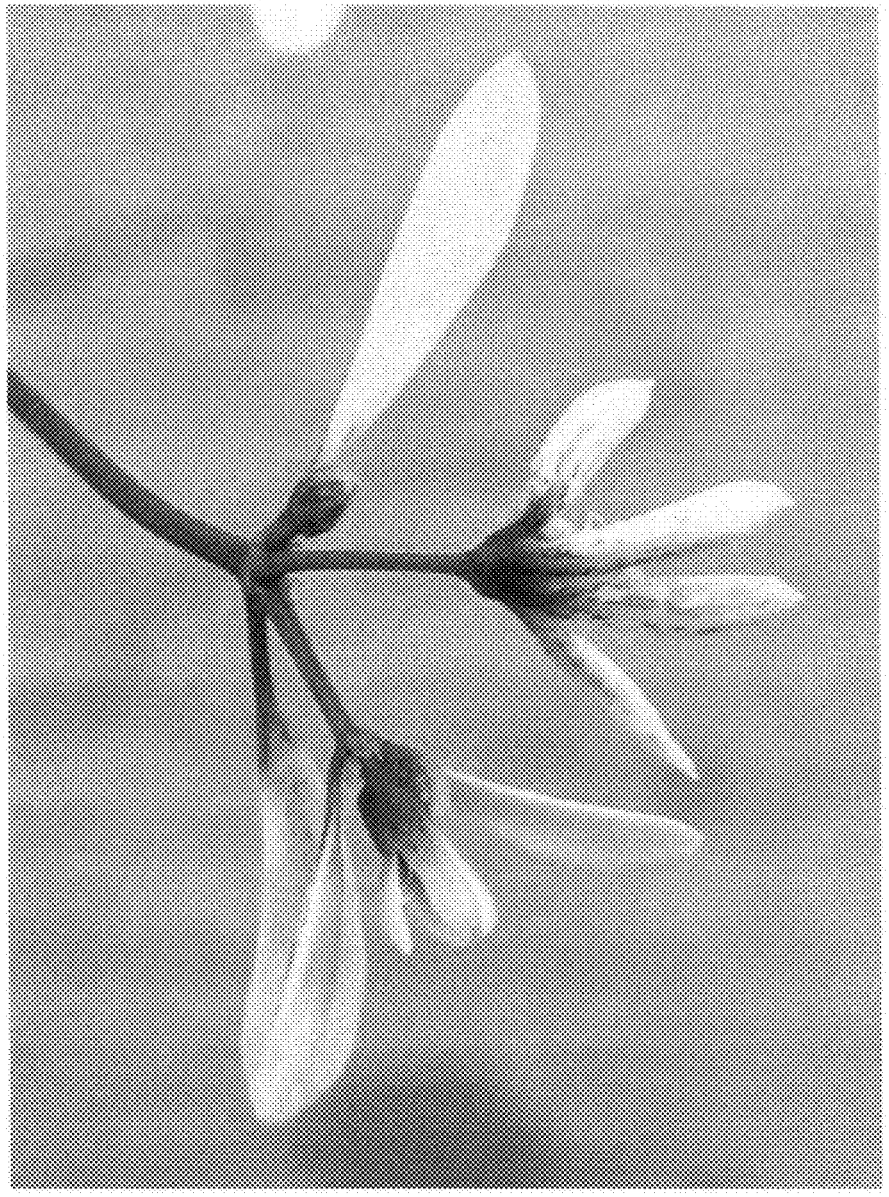

* * * * *